US010259635B2

(12) United States Patent
Ettlin et al.

(10) Patent No.: US 10,259,635 B2
(45) Date of Patent: Apr. 16, 2019

(54) APPARATUS AND METHODS FOR STORING AND MIXING SEPARATE SUBSTANCES

(71) Applicant: Sulzer Mixpac AG, Haag (CH)

(72) Inventors: Josef Ettlin, Eichberg (CH); Daniel Strasser, Gossau (CH); Cedric Ullmann, Engwang (CH)

(73) Assignee: SULZER MIXPAC AG, Haag (CH)

( * ) Notice: Subject to any disclaimer, the term of this patent is extended or adjusted under 35 U.S.C. 154(b) by 64 days.

(21) Appl. No.: 15/529,809

(22) PCT Filed: Nov. 25, 2015

(86) PCT No.: PCT/EP2015/077644
§ 371 (c)(1),
(2) Date: May 25, 2017

(87) PCT Pub. No.: WO2016/083451
PCT Pub. Date: Jun. 2, 2016

(65) Prior Publication Data
US 2017/0327296 A1 Nov. 16, 2017

(30) Foreign Application Priority Data

Nov. 28, 2014 (EP) .................................... 14195440

(51) Int. Cl.
*B65D 81/00* (2006.01)
*B65D 81/32* (2006.01)
(Continued)

(52) U.S. Cl.
CPC ......... *B65D 81/3255* (2013.01); *A45D 34/00* (2013.01); *A45D 40/24* (2013.01);
(Continued)

(58) Field of Classification Search
CPC .. B65D 81/3255; B65D 81/325; A61J 1/2006; A61J 1/2027; A61J 1/2093;
(Continued)

(56) References Cited

U.S. PATENT DOCUMENTS 2,153,594 A 6/1934 Saffir
3,380,451 A 4/1968 Porter et al.
(Continued)

FOREIGN PATENT DOCUMENTS

DE 20022899 U1 3/2002
DE 20314688 U1 11/2003
(Continued)

OTHER PUBLICATIONS

Extended European Search Report dated Jun. 11, 2015 in corresponding European Patent Application No. 14195440.4, filed Nov. 28, 2014.
(Continued)

*Primary Examiner* — Anshu Bhatia
(74) *Attorney, Agent, or Firm* — Global IP Counselors, LLP

(57) ABSTRACT

A storage and mixing device includes a mixing compartment, two pistons that each extend from the mixing compartment and end in a displacement section, each piston defining a passageway having a first opening communicating with the mixing compartment and a second opening communicating with an inlet at the displacement section, and a housing having two piston guides and a cartridge compartment connected to the piston guide, each piston guide slidably receiving one of the pistons, and each cartridge compartment receiving a removable cartridge that includes a cavity for containing separate substances and an opening sealed by a cartridge seal. The displacement section of each piston includes a piercing member for piercing the
(Continued)

cartridge seal of the cartridge arranged in the corresponding cartridge compartment, such that the displacement section enters the cartridge cavity and displaces the contained substance into the mixing compartment via the inlet and the passageway.

20 Claims, 6 Drawing Sheets

(51) Int. Cl.

| | | |
|---|---|---|
| *A61M 5/24* | (2006.01) | |
| *A61J 1/20* | (2006.01) | |
| *B01F 13/00* | (2006.01) | |
| *B01F 15/00* | (2006.01) | |
| *B01F 15/02* | (2006.01) | |
| *A61M 5/19* | (2006.01) | |
| *A45D 34/00* | (2006.01) | |
| *A45D 40/24* | (2006.01) | |
| *A61C 19/00* | (2006.01) | |
| *A61M 35/00* | (2006.01) | |
| *A61C 3/00* | (2006.01) | |
| *A61C 5/64* | (2017.01) | |
| *A61C 5/68* | (2017.01) | |
| *B29C 45/26* | (2006.01) | |

(52) U.S. Cl.
CPC .......... *A61C 19/005* (2013.01); *A61J 1/2006* (2015.05); *A61J 1/2027* (2015.05); *A61J 1/2093* (2013.01); *A61M 5/19* (2013.01); *A61M 5/2429* (2013.01); *A61M 5/2448* (2013.01); *B01F 13/0023* (2013.01); *B01F 15/0087* (2013.01); *B01F 15/0212* (2013.01); *B01F 15/0226* (2013.01); *B01F 15/0237* (2013.01); *B65D 81/325* (2013.01); *A45D 2034/005* (2013.01); *A61C 3/005* (2013.01); *A61C 5/64* (2017.02); *A61C 5/68* (2017.02); *A61M 35/003* (2013.01); *B01F 2215/006* (2013.01); *B01F 2215/0031* (2013.01); *B01F 2215/0032* (2013.01); *B01F 2215/0034* (2013.01); *B29C 45/26* (2013.01)

(58) Field of Classification Search
CPC .. A45D 2034/005; A45D 34/00; A45D 40/24; A61C 3/005; A61C 19/005; A61C 5/68; A61C 5/64; A61M 35/003; A61M 5/19; A61M 5/2429; A61M 5/2448; B01F 2215/0031; B01F 2215/0032; B01F 2215/0034; B01F 2215/006; B01F 13/0023; B01F 15/0087; B01F 15/0212; B01F 15/0226; B01F 15/0237; B29C 45/26

See application file for complete search history.

(56) References Cited

U.S. PATENT DOCUMENTS

| | | |
|---|---|---|
| 3,494,359 A | 2/1970 | Zackheim |
| 3,685,514 A | 8/1972 | Cheney |
| 3,914,419 A | 10/1975 | Haeger et al. |
| 4,254,768 A | 3/1981 | Ty |
| 4,676,655 A | 6/1987 | Handler |
| 4,801,009 A | 1/1989 | Amos |
| 5,161,715 A | 11/1992 | Giannuzzi |
| 5,370,273 A | 12/1994 | Rohloff et al. |
| 5,383,864 A | 1/1995 | Van Den Heuvel |
| 5,429,603 A | 7/1995 | Morris |
| 5,637,087 A | 6/1997 | O'Neil et al. |
| 5,667,102 A | 9/1997 | Keller |
| 5,788,670 A | 8/1998 | Reinhard et al. |
| 6,547,101 B1 | 4/2003 | Sogaro |
| 6,648,852 B2 | 11/2003 | Wirt et al. |
| 8,544,683 B2 | 10/2013 | Springhorn et al. |
| 8,561,845 B2 | 10/2013 | Reidt et al. |
| 2002/0087122 A1 | 7/2002 | Sogaro |
| 2004/0110112 A1* | 6/2004 | Xie .............. A61C 9/0026 433/89 |
| 2011/0114668 A1 | 5/2011 | Bublewitz et al. |

FOREIGN PATENT DOCUMENTS

| | | |
|---|---|---|
| EP | 1188455 A1 | 3/2002 |
| WO | 9531137 A1 | 11/1995 |

OTHER PUBLICATIONS

International Search Report dated Feb. 17, 2016 in corresponding International Application No. PCT/EP2015/077644, filed Nov. 25, 2015.
International Preliminary Report on Patentability and Written Opinion dated May 30, 2017 in corresponding International Application No. PCT/EP2015/077644, filed Nov. 25, 2015.

* cited by examiner

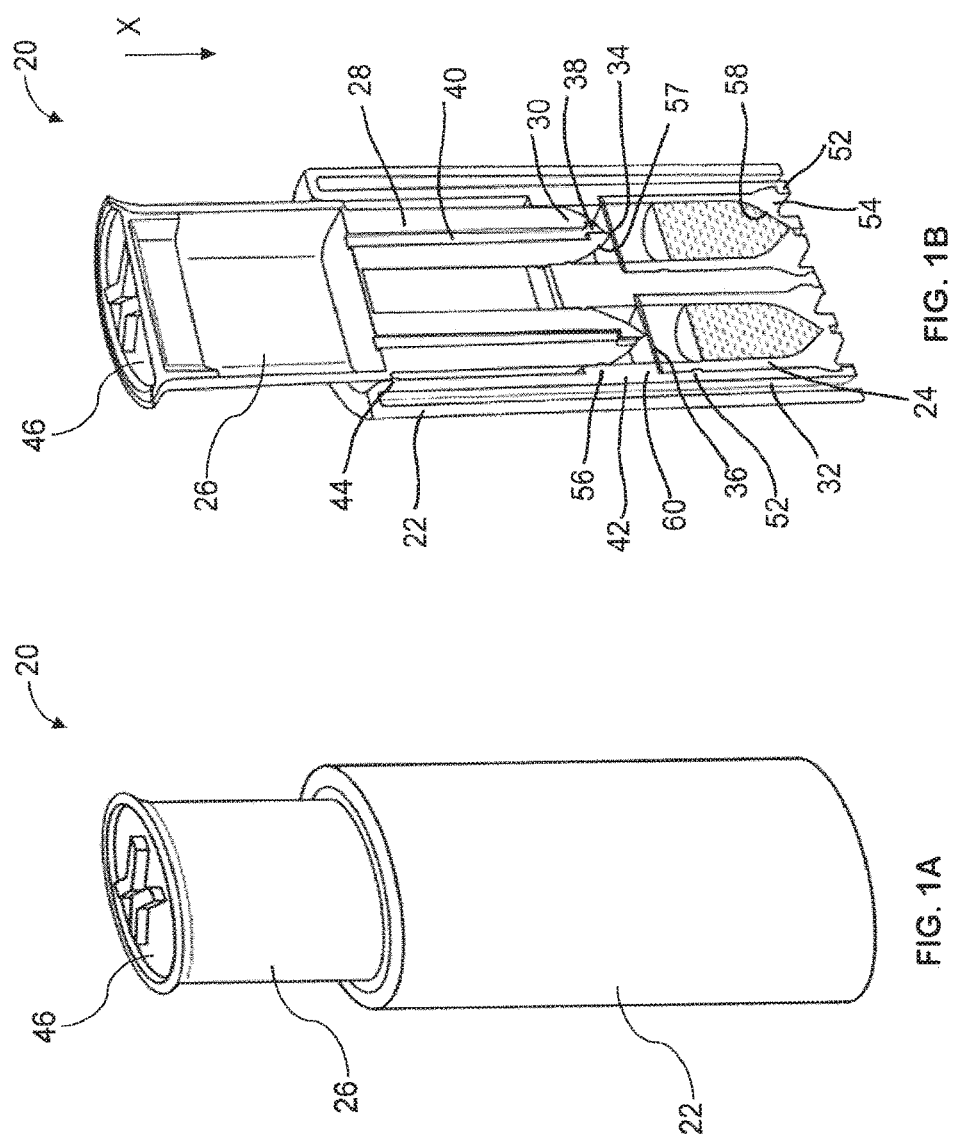

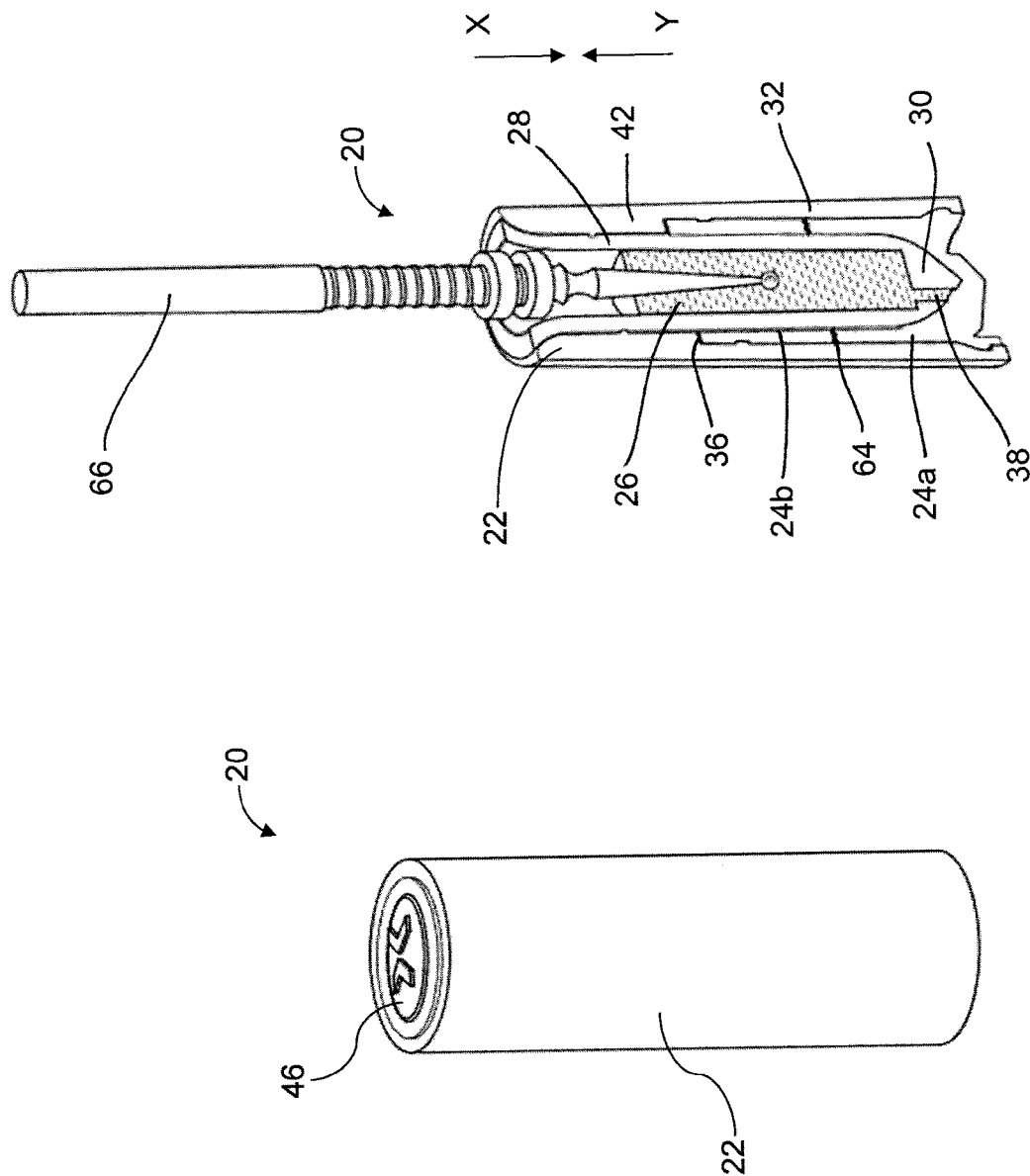

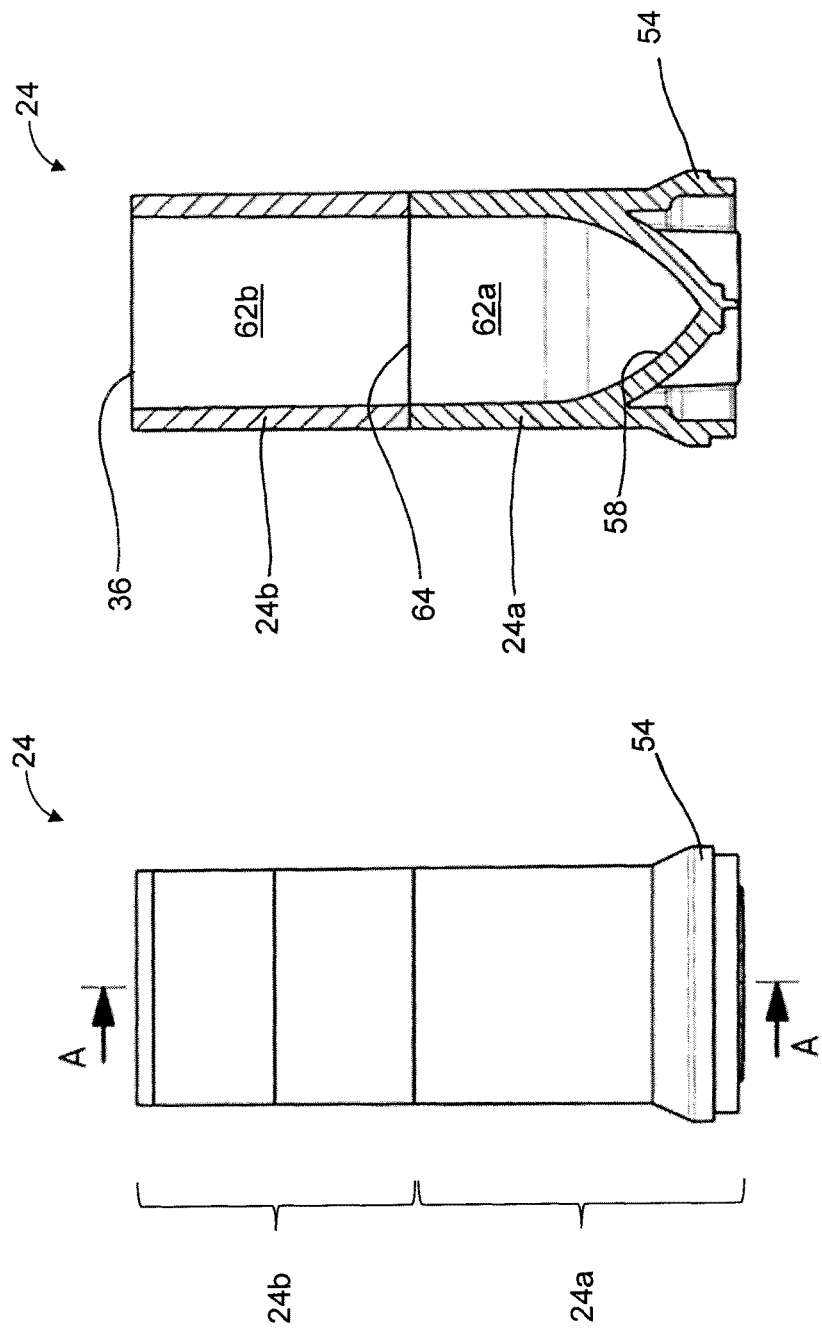

APPARATUS AND METHODS FOR STORING AND MIXING SEPARATE SUBSTANCES

CROSS-REFERENCE TO RELATED APPLICATIONS

This application is a U.S. National Stage application of International Application No. PCT/EP2015/077644, filed Nov. 25, 2015, which claims priority to European Patent Application No. 14195440.4, filed Nov. 28, 2014, the contents of each of which are hereby incorporated herein by reference.

BACKGROUND

Field of Invention

The present invention relates to devices for storing and for mixing together separate substances and to methods of operating such devices.

Background Information

Many medical and dental procedures involve the use of a preparation having a short shelf-life, i.e. that is unfit for use after a brief window of time. It is therefore impractical, uneconomical or sometimes even infeasible to store such a preparation in a ready-to-use state. Accordingly, such preparations are mixed at the time of use from stable substances that are each stored in individual packaging.

Generally, the mixture is prepared by transferring the separate substances from their packaging into a mixing vessel in which the substances are mixed together. However, first transferring the substances into the mixing vessel and then the finished mixture out of the mixing vessel can lead to product waste. Furthermore, both the transfer and mixing steps may be messy and time-consuming.

Some of these aspects can be addressed by storing the separate substances in an appropriately modified mixing vessel, thus eliminating the transfer step. However, the mixing vessel is oftentimes made of plastic, which may react with the substances and reduce their storage-life.

SUMMARY

Thus, there remains a need for improved devices and methods for storing and mixing two or more separate substances.

In the present invention, devices and methods are provided in which the substances are initially stored in one or more sealed removable cartridges, and at least one piston dispenses the at least one substance contained in each cartridge into a mixing chamber for mixing the substances at a time of use. The devices and methods may be used to conveniently prepare a medical, dental, pharmaceutical, cosmetic, adhesive or veterinary preparation on demand.

A first aspect of the invention is a storage and mixing device which stores each substance in a separately sealed cartridge and which comprises a piston corresponding to each cartridge to dispense the stored substance into a mixing compartment connected to the pistons.

Specifically the storage and mixing device comprises a mixing compartment, at least two pistons that each extend from the mixing compartment and end in a displacement section, wherein each piston defines a passageway having a first opening that communicates with the mixing compartment and a second opening that communicates with an inlet provided at the displacement section, and a housing having at least two pairs of a piston guide and a cartridge compartment connected to the piston guide, each piston guide slidably receiving one of the pistons, and each cartridge compartment receiving a removable cartridge that comprises a cavity for containing one of the separate substances and an opening sealed by a cartridge seal, wherein the displacement section of each piston further comprises a piercing means or member for piercing the cartridge seal of the cartridge arranged in the corresponding cartridge compartment, such that the displacement section can enter the cartridge cavity and displace the contained substance into the mixing compartment via the inlet and the passageway of the piston.

The first aspect covers devices having more than two cartridges provided the device comprises a number of pistons corresponding to the number of cartridges. However, for the sake of simplicity, the following refers to a device having two pistons and two substances, each stored in a separate cartridge. In particular, each sealed cartridge is initially loaded into a corresponding cartridge compartment formed at a device housing. The device can then be stored in this state during the shelf-life of the substances.

In order to create the mixture, the pistons are configured to be movable relative to the housing and toward the cartridge compartments, e.g. when pressure is applied to the connected mixing compartment. Once the piercing member of the displacement section has come into contact and pierced the cartridge seal sealing the opening of the cartridge cavity, the piston guide continues to guide the piston toward the cartridge compartment, and the displacement section of the piston enters the cartridge cavity, displacing the substance stored in the cavity into the inlet of the displacement section. As the piston continues further into the cartridge cavity, the substance is displaced further along the passageway of the piston until it reaches the mixing compartment. When both substances have been displaced into the mixing compartment in this way, the substances can mix together to form the desired mixture.

Thus, this aspect of the present invention enables the stable storage and mixing of a multi-part mixture in a single device. The piston is able to thoroughly dispense the respective substance from the cartridge, which leads to a reduction in waste. Furthermore, since the cartridges are removable, the material of both the cartridges and the mixing compartment can be chosen with regards to the stored substances and or the final mixture. Accordingly, cartridge materials can be selected which are able to prolong the shelf-life of the stored substances.

Optionally, the at least two pistons can extend from the mixing compartment parallel to one another so the substances can be simultaneously dispensed from their respective cartridges by a single movement.

Additionally, the passageways of the pistons may be configured to have a substantially smaller volume than the storage capacity of the cartridge cavity. Accordingly, when the displacement section of the piston fully occupies the cartridge cavity and displaces the stored substance into its inlet and passageway, only a small amount of the substance or mixture remains in the inlet and passageway.

A second aspect of the invention is a storage and mixing device that differs from the previously described device in that the substances are stored in sealed partitions of a single cartridge.

Specifically, the storage and mixing device comprises a piston having a displacement section arranged at one end, wherein the piston defines a mixing compartment that communicates with an inlet provided at the displacement section, and a housing having a piston guide and a cartridge compartment connected to the piston guide, the piston guide slidably receiving the piston in a sliding direction, and the cartridge compartment receiving a removable cartridge that comprises a cavity for containing at least two separate substances and an opening sealed by a cartridge seal, wherein the cartridge cavity comprises one or more inner membranes that partition the cavity into two or more sealed partitions arranged adjacently in the sliding direction, each of which stores one of the separate substances, wherein the displacement section of the piston further comprises a piercing member for piercing first the cartridge seal and then the one or more inner membranes of the cartridge, such that the displacement tip can enter the cartridge cavity and displace the contained substances into the mixing compartment via the inlet of the displacement section.

Accordingly, during the mixing step, the piercing member of the displacement section pierces the cartridge seal and then breaks the one or more inner membranes of the cartridge to combine the substances stored in the separate partitions of the cartridge. This resulting mixture is then displaced by the displacement section into the mixing compartment. This aspect of the present invention results in a compact device for storing and mixing separate substances.

In accordance with either the first or the second aspect of the present invention, the at least one piston guide may comprise a sealing member that forms a seal with an outer surface of the piston received in the piston guide. The resulting seal ensures that the substance stored in the cartridge cavity is completely displaced into the inlet of the displacement section. A complete displacement of the substance out of the cartridge cavity and into the displacement section of the piston is also provided when an end face of the displacement section is configured to mate with a corresponding bottom surface of the cartridge cavity. This mating arrangement causes the displacement section to occupy the entire volume of cartridge cavity, thus displacing the substance to the greatest extent possible.

An arrangement in which the displacement section of the piston fully occupies the cartridge cavity is also provided when a maximum outer width of the displacement section corresponds substantially to a maximum inner width of the cartridge cavity. Given, for example a cylindrical piston and a substantially cylindrical cartridge cavity, this would mean that the width or outer diameter of the piston is substantially equal to the width of the cartridge cavity.

The piercing member of the displacement section can be formed by a sharp tip to easily pierce a cartridge seal, in particular if the inlet of the displacement section does not coincide with the piercing tip. The one or more cartridge seals can also be easily pierced if the corresponding cartridge compartment comprises one or more retaining members to engage and secure the cartridge in the cartridge compartment. The securing through the retaining member counteracts the force exerted by the piercing tip on the cartridge seal and facilitates piercing. The one or more retaining members also ensure that the cartridges are securely installed during storage and do not, for example, fall out of the device housing. Examples of suitable retaining members are collars or notches formed at an inner surface of the cartridge compartment and which engage with the outer surface of the received cartridge.

Optionally, the device housing further comprises a locking member that engages an outer surface of the mixing compartment and prevents the piercing member of the displacement section from piercing the corresponding cartridge seal while the device is being stored, i.e. before the intended mixing of the substances.

The mixing compartment may further comprise a removable closure cap that makes it possible to shake the device to agitate and better mix the substances in the mixing compartment.

A third aspect of the invention is a mold, in particular an injection mold, for molding any one of the parts of a storage and mixing device according to the first or the second aspect of the invention.

Specifically, the mold comprises a first and a second mold segment that abut to form a mold cavity, at least part of which corresponds in shape to a housing or a piston of a storage and mixing device according to the first or the second aspect of the invention.

For an injection mold, this could mean that the mold cavity formed by the mold segments corresponds to an arrangement of multiple device housings to be molded in a single step using, for example, polypropylene or polyethylene. In fact, the manufacturing costs for the storage and mixing device are reduced if both the piston and the housing are manufactured by injection molding.

A fourth aspect of the invention is a method for storing separate substances and then mixing these substances using any of the devices described above.

Specifically, the method comprises the steps of: loading a cartridge containing at least one substance in each of the one or more cartridge compartments; applying pressure to a section of the mixing compartment remote from the displacement section of at least one piston to effect movement of the at least one piston relative to the housing and in a first direction; piercing the at least one cartridge seal of the cartridge with the piercing member of the displacement section of the at least one piston; and continuing to effect movement of the at least one piston in the first direction until an end face of the displacement section of the piston meets an inner surface of the cartridge cavity arranged opposite to the cartridge opening such as to effect movement of the at least one substance stored in the cartridge in a second direction opposite the first direction and into the mixing compartment via the inlet of the displacement section.

Following the step of loading the one or more cartridges into respective cartridge compartments of the device housing, the device may optionally be stored for a period of time that is shorter than the shelf life of the substances. Alternatively, the substances can immediately be mixed together after the cartridges have been loaded. For a mixture requiring agitation for the substances to react with one another, the method may comprise an additional step after the end face of the displacement section of the piston has met the inner surface of the cartridge cavity which includes shaking the device and then removing a removable closure cap of the mixing compartment to retrieve the finished mixture using, for example, a separate applicator.

BRIEF DESCRIPTION OF THE DRAWINGS

Referring now to the attached drawings which form a part of this original disclosure.

FIGS. 1A and 1B show an embodiment of a device in accordance with the first aspect of the present invention in a storage state;

FIGS. 5A and 5B show the embodiment of FIGS. 4A and 4B in a mixing state; and

FIGS. 6A and 6B show the cartridge of FIGS. 4A through 5B.

DETAILED DESCRIPTION OF THE EMBODIMENTS

Figure 2B:
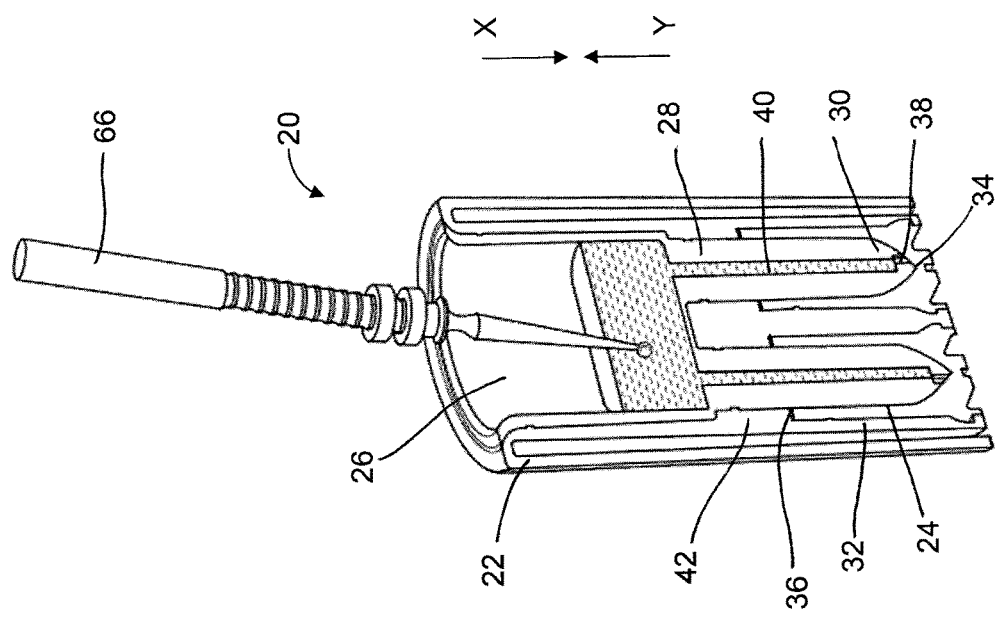
FIGS. 2A and 2B show the embodiment of FIGS. 1A and 1B in a mixing state.

Referring to the figures, wherein like numerals indicate corresponding parts throughout the several views and aspects of the invention, a storage and mixing device 20 for separate substances (hereinafter 'device') comprises a housing 22 for storing one or more cartridges 24, each of which contains at least one substance. The substances can be fluids, gels or the like and are mixed together to form a mixture such as medical, dental, pharmaceutical, cosmetic, adhesive or veterinary preparation. Each substance is dispensed into a mixing compartment 26 by a piston 28, in particular, displaced into the mixing compartment 26 by a displacement section 30 formed at the end of the piston 28. The housing 22 and the one or more pistons 28 can be made of a material comprising polypropylene or polyethylene.

Turning to the embodiment shown in FIGS. 1A through 2B, the device 20 comprises two sealed cartridges 24 and a piston 28 corresponding to each cartridge 24 to dispense a stored substance into a mixing compartment 26. The mixing compartment 26 is connected to the pistons 28. In the storage state of the device 20, shown in FIGS. 1A and 1B, each cartridge 24 is loaded into a corresponding cartridge compartment 32 of the device housing 22. In other words, the substances are kept sealed and separate from one another and have not yet been mixed. Accordingly, the device makes it possible to store the substances for a longer amount of time than the mixture itself could be stored.

Figure 3B:
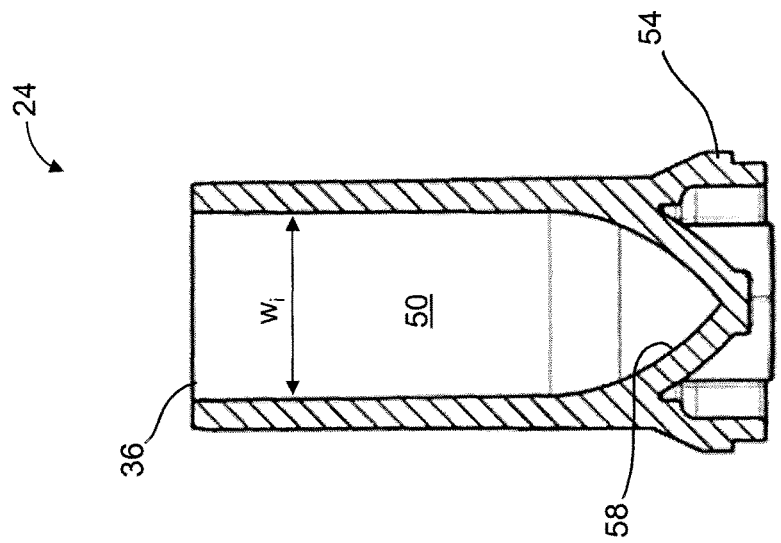
FIGS. 3A and 3B show the cartridge of FIG. 1A through FIG. 2B.
Figure 3A:
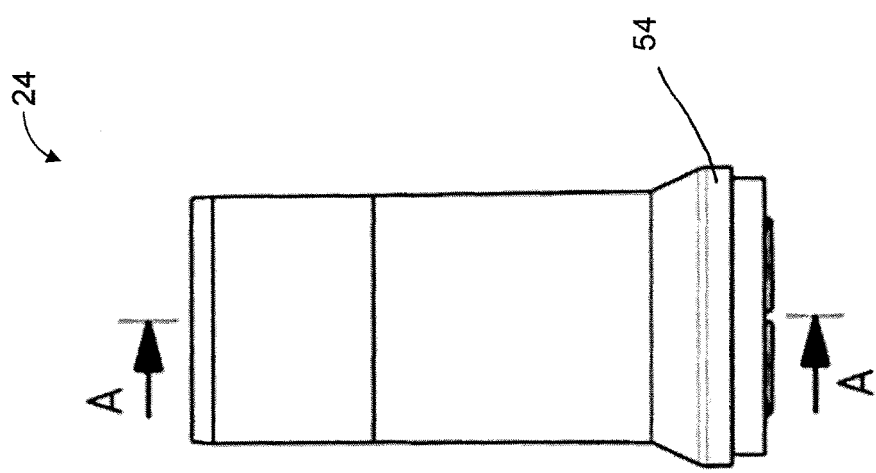

The cartridges 24, which are show in detail in FIGS. 3A and 3B, are generally installed during the manufacture of the device 20 so that a fully assembled device 20 can be delivered. However, it is also conceivable for the user to load the cartridges 24 required to form the desired mixture. A material can be selected for cartridge 24 that is most compatible with the stored substance, such as cyclic olefin copolymer (COC), so that the storage life of the substance is not shortened by a reaction to the cartridge material. A cartridge cavity 50 for containing the substance can be created, for example, by injection molding, and then filled with the substance. A cartridge seal 36 for sealing the cartridge cavity 50 can then be welded on.

The two pistons 28 extend in parallel from the mixing compartment 26 and end in a displacement section 30 for displacing the substance stored in the cartridge 24. The displacement section 30 includes a piercing means or member 34 for piercing the cartridge seal 36 and an inlet 38 into which the substance can be displaced. The extent of the piston 28 also defines a passageway 40 that connects the inlet 38 of the displacement section 30 to the mixing compartment 26. In the storage state of the device 20, the displacement sections 30 of the pistons 28 are each slidably supported in a piston guide 42 that is arranged adjacent to and communicates with a respective cartridge compartment 32.

In the storage state, the piercing member 34 of each displacement section 30 may rest on or slightly above the cartridge seal 36 of the corresponding cartridge 24. To prevent the pistons 28 and their respective displacement sections 30 from moving toward the cartridges 24 and piercing the cartridge seals 36, the device housing 22 comprises a locking member 44 that engages an outer corner of the mixing compartment 26.

To transition from the storage to the mixing state, pressure is applied to the mixing compartment 26, for example, at a closure cap 46. Once the locking force of the locking member has been overcome, the parallel pistons 28 begin to slide in unison along the piston guides 42, i.e. in a first direction X relative to the housing 22, and toward their respective cartridges 24. In this context, friction and/or adhesion between the pistons 28 and the piston guides 42 can be reduced by manufacturing the device housing 22 and the pistons 28 from different materials, such as polypropylene and polyethylene respectively.

In the illustrated embodiment, the piercing member 34 of each displacement section 30 is formed as a sharp tip which pierces the cartridge seal 36 that seals an opening of the cartridge cavity 50 for receiving the stored substance. However, other configurations of the piercing member, such as a sharp annular edge, are also possible. By forming the inlet 38 of the displacement section 30 adjacent to, but not coinciding with, the piercing tip 34, the piercing tip 34 is made particularly sharp. To make piercing the cartridge seals 36 easier, each cartridge compartment 32 also comprises two retaining members 52 to engage and stabilize the cartridge. A first retaining member 52 is a formed by a notch adjacent to the piston guide 42 that engages an outer cartridge surface. A second retaining member 52 is formed by a collar that encircles a base 54 of the cartridge 24 (FIGS. 3A and 3B).

Once the cartridge seal 36 has been pierced, the piston guide 42 continues to guide the piston 28 toward the cartridge compartment 32 in the first direction X, so that the displacement section 30 of the piston 28 enters a cartridge cavity 50 (FIG. 3B) and displaces the substance stored in the cavity 50 into the inlet 38 of the displacement section 30 in a second direction Y that is opposite the first direction X.

As the piston 28 further enters the cartridge cavity 50, an increasing amount of the substance is displaced into the passageway 40 of the piston 28 until the substance reaches the mixing compartment 26. In order to ensure that the displaced substance flows into the inlet 38 as opposed to through a gap between the piston 28 and the piston guide 42, the piston guide 42 comprises a sealing member 56 that forms a seal with an outer surface of the piston 28. In the illustrated embodiment, the sealing member 56 is formed by a projection provided at an inner wall of the piston guide 42. Alternatively or additionally, a sufficient sealing effect may be provided by a sufficiently elastic cartridge seal 36 that hugs the outer surface of the piston 28 after being pierced.

Figure 2A:
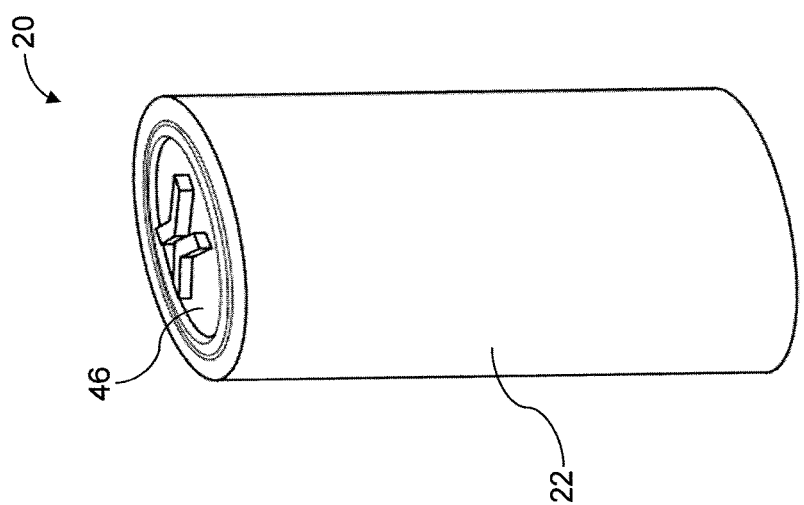

When both substances have been displaced into the mixing compartment 26, the substances can mix together to form the desired mixture, as shown in the final, ready-to-use state of FIGS. 2A and 2B. In this state, the closure cap 46 can be removed so that the prepared mixture can be taken from the mixing compartment 26 using, for example, a separate applicator 66. Since it is difficult to access the mixture remaining in the inlets 38 and passageways 40 using the applicator 66, it is desirable to configure the inlets 38 and passageways 40 to be as small as possible, so that as much of the mixture is displaced to the mixing compartment 26 as possible. This is the case when a volume of the passageway 40 is substantially smaller than the storage capacity of the cartridge cavity 50, with the storage capacity, i.e. the volume of the cartridge cavity 50, ranging for example from 0.3 to 10 ml. For a piston 28 having a particular length, this translates to a passageway 40 that is substantially narrower than the piston 28.

In the illustrated embodiment, a thorough displacement or removal of each substance into the mixing compartment 26, is provided when the displacement section 30 of the piston 28 occupies the entire volume of the cartridge cavity 50 in the mixed state. One reason for this is that an end face 57 of the displacement section 30 that faces a bottom surface 58 of the cartridge cavity 50 is configured to mate with the cartridge cavity 50.

A further reason is that a maximum width of the displacement section 30 corresponds substantially to a maximum inner width $w_i$ of the cartridge cavity 50 (FIG. 3B). Furthermore, the widths of the piston 28, piston guide 42 and cartridge opening are substantially equal. As the cartridge compartment 32 is configured to accommodate the outer width of the cartridge, the housing 22 forms an annular shoulder 60 between each cartridge compartment 32 and adjacent piston guide 42. When the cartridge 24 is inserted into the cartridge compartment 32, the cartridge seal 36 is secured between the shoulder 60 and the remainder of the cartridge 24, making the cartridge seal 36 easier to pierce.

Figure 4B:
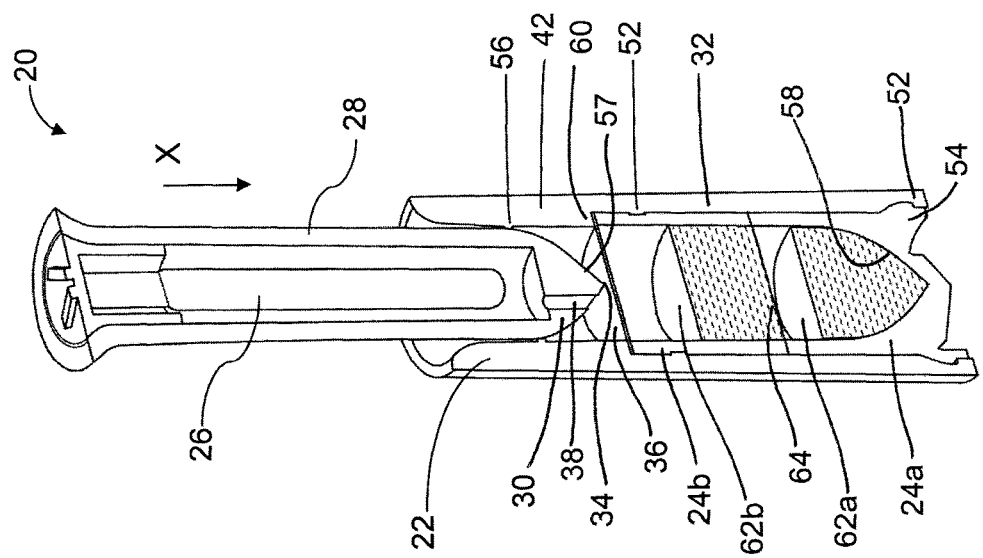
FIGS. 4A and 4B show an embodiment of a device in accordance with the second aspect of the present invention in a storage state.
Figure 4A:
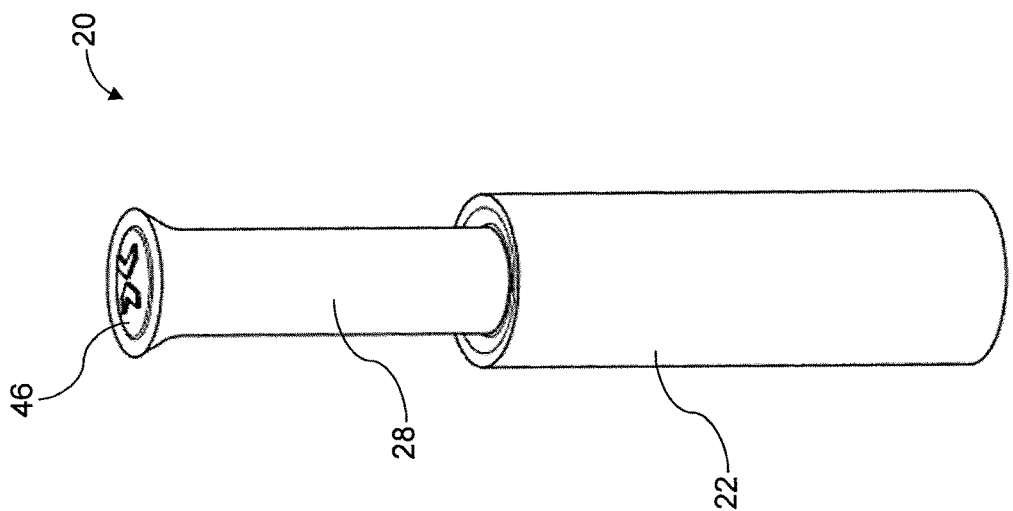

FIGS. 4A and 4B show a device 20 in accordance with a further aspect of the present invention that is described in terms of its differences to the device 20 shown in FIGS. 1A through 2B. In particular, the device 20 comprises a single piston 28 and single removable cartridge 24 that stores the substances in separate, sealed partitions 62 of the same cartridge 62.

Accordingly, a device housing 22 comprises one cartridge compartment 32 for receiving the sealed cartridge 24 and one piston guide 42 connected to the cartridge compartment 32. In addition to a cartridge seal 36 sealing an opening to a cartridge cavity 50, the cartridge 24 comprises one or more inner membranes 64 that partition the cartridge cavity 50 into two or more sealed partitions 62 (FIG. 6B). The inner membranes 64 are arranged in such a way that when the cartridge 24 is inserted into the cartridge compartment 32, the sealed partitions 62 are arranged serially, i.e. one after another, with respect to the piston guide 42.

In the device 20 of FIGS. 4A through 5B, the one piston 28 defines both a longitudinal mixing compartment 26 and a displacement section 30 for displacing the substances stored in the individual partitions of the cartridge. The displacement section 30 includes a piercing member 34 for piercing the cartridge seal 36 and inner membranes 64, as well as an inlet 38 that is connected to the mixing compartment 26 and displaces the substances stored in the cartridge into it. In contrast to the device of FIGS. 1A through 2B, the mixing compartment 26 is directly connected to the inlet 38 of the displacement section 30 as opposed to via a passageway.

The one piston 28 is slidably received in the one piston guide 42, which guides the displacement section 30 of the piston 28 toward the cartridge compartment 32. When the piston 28 is moved relative to the device housing 22, the piercing tip 34 of the displacement section 30 first makes contact with and pierces the cartridge seal 36 that seals an opening of the cartridge cavity 50. The piercing of the cartridge seal 36 allows the displacement section 30 to move into the first partition of the cartridge cavity 50 and displace the substance stored in the first partition into the mixing compartment 26 via the inlet 38 of the displacement section 30.

As the piston 28 continues to move relative to the housing 22, the piercing tip 34 of the displacement section 30 then makes contact with and pierces the at least one inner membrane 64. This enables the displacement section 30 to move into and displace the substance stored in the next partition of the cartridge cavity 50 into the mixing compartment 26. As the piston 28 moves further into the cartridge cavity 50, an increasing amount of the substances is displaced into the mixing compartment 26 until an end face 57 of the displacement section 30 reaches a bottom surface 58 of the cartridge cavity 50, as shown in FIGS. 5A and 5B.

As shown in FIGS. 6A and 6B, one way of forming the cartridge 24 with its multiple partitions 62 is to fill a first cartridge section 24a with a first substance and then seal the first cartridge section 24a with an inner membrane 64, thus forming a first partition 62a. Next, a second cartridge section 24b is welded onto the first cartridge section 24a and filled with a second substance. The second cartridge section 24b is then sealed with the cartridge seal 36 to form a second partition 62b. The combined cartridge sections 24a and 24b thus form the cartridge 24 as a whole, while the partitions 62a, 62b correspond to the cartridge cavity 50. In this context, the cartridge sections 24a, 24b can be made of a material comprising cyclic olefin copolymer (COC) and by injection molding. Although the inner membrane 64 and cartridge seal 36 are described as separate parts, it is appreciated that they can be made of the same type of material.

The invention claimed is:

1. A storage and mixing device for separate substances comprising:
    a mixing compartment;
    at least two pistons, each piston of the at least two pistons extending from the mixing compartment and ending in a displacement section, and defining a passageway having a first opening that communicates with the mixing compartment and a second opening that communicates with an inlet at the displacement section; and
    a housing having at least two piston guides and a cartridge compartment of at least two cartridge compartments connected to each piston guide of the piston guides, each piston guide of the piston guides slidably receiving a piston of the at least two pistons, and each cartridge compartment of at least two cartridge compartments configured to receive a removable cartridge of at least two removable cartridges, each removable cartridge comprising a cavity containing one of the separate substances and an opening sealed by a cartridge seal,
    the displacement section of each piston of the at least two pistons further comprises a piercing member configured to pierce the cartridge seal of the removable cartridge of the at least two removable cartridges arranged in a corresponding cartridge compartment, such that the displacement section of each piston of the at least two pistons is capable of entering the cavity of the removable cartridge of at least two removable cartridges arranged in the corresponding cartridge compartment and displace the contained substance into the mixing compartment via the inlet and the passageway.

2. The storage and mixing device of claim 1, further comprising the at least two removable cartridges received in the cartridge compartments, the cavity of each cartridge containing the substance for forming a mixture.

3. The storage and mixing device of claim 2, wherein, for each piston and cartridge, the volume of the passageway of the piston is substantially smaller than a storage capacity of the cavity.

4. The storage and mixing device of claim 1, wherein the at least two pistons extend in parallel from the mixing compartment.

5. The storage and mixing device of claim 1, wherein the housing comprises a locking member that engages an outer surface of the mixing compartment.

6. The storage and mixing device of claim 1 wherein the mixing compartment comprises a removable closure cap.

7. A mold comprising:
   a first mold segment and a second mold segment that abut to form a mold cavity, at least part of the mold cavity corresponds in shape to the housing or the piston of the storage and mixing device according to claim 1.

8. The storage and mixing device of claim 1, wherein the at least one retaining members is a collar engaging a peripheral surface of the cartridge opposite from the opening of the cartridge or a projection arranged adjacent the piston guide connected to the cartridge compartment and engaging a corresponding notch at an outer surface of the cartridge.

9. The storage and mixing device of claim 2 wherein, for each piston of the at least two pistons and removable cartridge of the at least two removable cartridges arranged in a corresponding cartridge compartment, an end face of the displacement section of the piston matches an inner surface of the cavity arranged opposite to the opening in the removable cartridge.

10. The storage and mixing device of claim 2 wherein, for each piston of the at least two pistons and removable cartridge of the at least two removable cartridges arranged in a corresponding cartridge compartment, a width of the piston guide of the piston guides slidably receiving the piston and a width of the opening in the cartridge are substantially equal.

11. The storage and mixing device of claim 1, wherein each piston of the piston guides forms a seal with an outer surface of the piston of the at least two pistons slidably received in the piston guide by a sealing member.

12. A storage and mixing device for separate substances comprising:
   a piston having a displacement section arranged at one end, the piston defining a mixing compartment in communication with an inlet at the displacement section, and
   a housing having a piston guide and a cartridge compartment connected to the piston guide, the piston guide slidably receiving the piston in a sliding direction, and the cartridge compartment configured to receive a removable cartridge comprising a cavity containing at least two separate substances and an opening sealed by a cartridge seal,
   comprising at least one inner membrane partitioning the cavity into at least two sealed partitions arranged adjacently in the sliding direction, each sealed partition of the at least two sealed partitions storing one of the separate substances, and
   the displacement section of the piston further comprising a piercing member configured to first pierce the cartridge seal and then the at least one inner membrane of the cartridge such that a displacement tip is capable of entering the cartridge cavity and displace the contained substances into the mixing compartment via the inlet of the displacement section.

13. The storage and mixing device of claim 12 further comprising the cartridge received in the cartridge compartment, the cavity of the cartridge comprising the at least two sealed partitions, each sealed partition of the at least two sealed partitions containing a substance of the separate substances for forming a mixture.

14. The storage and mixing device of claim 13 wherein, for the piston and cartridge, an end face of the displacement section of the piston matches an inner surface of the cartridge cavity arranged opposite to the opening in the cartridge.

15. The storage and mixing device of claim 13 wherein, for the piston and cartridge, a width of the piston guide and a width of the opening in the cartridge stored in the cartridge compartment are substantially equal.

16. The storage and mixing device of claim 12, wherein the piston guide forms a seal with an outer surface of the piston slidably received in the piston guide by a sealing member.

17. The storage and mixing device of claim 12, wherein the displacement tip does not coincide with the inlet of the displacement section of the piston.

18. The storage and mixing device of claim 12, wherein the cartridge compartment comprises at least one retaining members configured to engage an outer surface of the cartridge.

19. A method of mixing a first and a second substance, using the storage and mixing device of claim 1, the method comprising:
   loading a respective cartridge containing at least one substance in each of the cartridge compartments;
   applying pressure to a section of the mixing compartment remote from the displacement section of each piston to effect movement of each piston relative to the housing and in a first direction;
   piercing the cartridge seal of the respective cartridge with the piercing member of the displacement section of each piston;
   continuing to effect movement of each piston in the first direction until the end face of the displacement section of each piston meets an inner surface of the cavity of the respective cartridge arranged opposite to the opening such as to effect movement of the substance stored in the respective cartridge in a second direction opposite the first direction and into the mixing compartment via the inlet of the displacement section.

20. The method of claim 19, wherein the first and second substances are mixed to create a medical, dental, pharmaceutical, cosmetic, adhesive or veterinary preparation.

\* \* \* \* \*